United States Patent [19]

Beaubiah

[11] Patent Number: 5,400,782
[45] Date of Patent: Mar. 28, 1995

[54] INTEGRAL MEDICAL ELECTRODE INCLUDING A FUSIBLE CONDUCTIVE SUBSTRATE

[75] Inventor: Michael K. Beaubiah, Kingston, Canada

[73] Assignee: Graphic Controls Corporation, Buffalo, N.Y.

[21] Appl. No.: 957,996

[22] Filed: Oct. 7, 1992

[51] Int. Cl.⁶ .............................. A61B 5/04
[52] U.S. Cl. ........................ 128/640; 128/641; 607/152
[58] Field of Search ............... 128/639–641, 128/643–644, 798, 802–803, 783; 607/129, 152–153

[56] References Cited

U.S. PATENT DOCUMENTS

| | | | |
|---|---|---|---|
| 4,274,420 | 6/1981 | Hymes | 128/641 |
| 4,674,512 | 6/1987 | Rolf | 128/640 |
| 4,692,273 | 9/1987 | Lawrence | 128/640 X |
| 4,722,761 | 2/1988 | Cartmell et al. | 128/640 X |
| 4,848,348 | 7/1989 | Craighead | 128/639 |
| 5,002,792 | 3/1991 | Vegoe | 128/639 X |
| 5,269,810 | 12/1993 | Hull et al. | 128/639 X |

Primary Examiner—Angela D. Sykes
Attorney, Agent, or Firm—Ratner & Prestia

[57] ABSTRACT

An integral medical electrode for monitoring and diagnostic applications which includes a fusible conductive substrate to which are fused the other components, such as the conductor, of the electrode. The fusible conductive substrate includes a non-conductive carrier providing a support layer; a conductive additive; and a sealant functioning as a fusible bonding medium to integrate the non-conductive carrier, the conductive additive, and the other components of the electrode.

31 Claims, 3 Drawing Sheets

INTEGRAL MEDICAL ELECTRODE INCLUDING A FUSIBLE CONDUCTIVE SUBSTRATE

FIELD OF THE INVENTION

The present invention relates generally to a skin-contacting medical electrode able to transmit low-power, bio-electric signals between the skin surface and an electrical conductor. More specifically, the present invention relates to a conductive substrate, which can be fused to compatible materials so that the various electrode components become integral parts of the substrate, and to a method of manufacturing an electrode using such a substrate.

BACKGROUND OF THE INVENTION

There are a variety of skin-contacting, medical electrodes able to transmit low-power, bio-electric signals between the skin surface and an electrical conductor. Such electrodes include those for monitoring and diagnostic purposes, sensing electrodes, transcutaneous electrical nerve stimulating (TENS) electrodes, iontophoretic electrodes, electromyographic (EMG) electrodes, and others. The present invention may be adapted to any of the various electrodes to provide an improved device.

1. Monitoring and Diagnostic Electrodes

The focus of the present invention, however, is on those skin-contacting electrodes which are used to measure bio-electric signals from the skin of a patient for medical monitoring and diagnostic applications. Various configurations exist for such medical or biomedical electrodes; the field is relatively crowded. The two most common types of monitoring and diagnostic electrodes are "stud"-type electrodes and tab-type or "studless" electrodes.

2. Stud-Type Electrodes

The stud-type electrodes generally have a non-conductive support layer (affixed to the skin by an adhesive) which provides support for the electrode. A conductor, positioned within or over the support layer, transmits the bio-electric signals from the skin. A metallic male fastener, or "stud," is mounted on the support layer via an eyelet and is electrically connected to the conductor.

A female, quick-disconnect, snap connector is located at one end of an electrical lead. On its other end, the lead is connected to monitoring or diagnostic equipment. The snap connector hooks, snaps, or otherwise engages the stud placed on the electrode to make electrical contact with that electrode and to transmit the bio-electric signals from the stud to the equipment. The hook or snap operation of the female snap connector is advantageous because it gives the operator (e.g., a nurse) affirmative assurance that connection to the electrode has been made; engagement creates a noticeable feel and, typically, an audible sound.

The stud-female snap connector type of connection is especially desirable for medical electrodes because it allows the electrode to be positioned on the patient and then easily connected or disconnected from its corresponding lead. For that reason, most monitors used by hospitals and clinics incorporate leads which have female snap connectors. The lead wire plus female snap connector requires, however, that the electrode which it engages have a conductive stud.

3. Tab-Type Electrodes

The second prevalent type of monitoring and diagnostic electrode is the tab electrode. The connector (typically an alligator clip) interconnects that second type of electrode by engaging the electrode itself, usually at a lateral extension or tab. An example of a monitoring and diagnostic electrode which avoids the use of a stud is disclosed in Canadian Patent No. 1,269,417 issued to Beaubiah and Moore.

One problem with the tab electrode is that, unlike the stud electrode, it typically does not permit rotation between the electrode and the connector. Rotation prevents the electrode from disengaging when the patient moves. Another problem is that tab electrodes cannot be readily connected to the female snap connector of the type in wide-spread use for making contact with the stud-containing electrodes. Still another problem is that the electrical signals transmitted by tab electrode assemblies tend to suffer from increased noise relative to their stud counterparts. Such undesirable noise is caused, at least in part, by the exposed metal of the connector. Accordingly, in view of the various drawbacks of the tab electrodes, the present invention focuses on the stud electrode.

4. General Considerations

In part because of the prevailing risks associated with transmission of infectious disease through medical instruments (sterility in the medical environment must be maintained), the expense of cleaning such instruments, and the necessity that the instruments be reliable in use (the electrode may be part of a life support system), medical electrodes used for monitoring and diagnostic purposes are often disposable: they are discarded after application to only one patient. Consequently, the cost to manufacture each electrode must be minimized. Even a savings of $0.0025 per electrode is of great importance. The manufacturing step of affixing the stud to the support layer, conventionally done by punching through an eyelet, constitutes a large part of the cost of manufacturing the stud electrode.

For medical electrodes and, more generally, for direct measurement of electrical signals, a continuous electrical path is required from the source of the signal to the equipment which monitors that signal. A simple path consists of wires contacting the signal source at one end and equipment inputs at the other. In practice, connectors (such as the medical electrode stud) are provided at both termination points of the path to ensure that a stable connection is maintained. Secondary connections may also be provided to extend the path through additional components along the signal path. Each termination point or extension thereof adds both cost and complexity to the circuit and also increases the potential for signal degradation through losses at the interface site or sites.

Because the separate components of the conventional electrodes are not integrally formed, there is an increased potential for signal degradation at interfaces. Moreover, signal integrity relies on the proximity of each of the components to each other.

Complex assemblies of medical electrodes require attachment of the many components described above and frequently use manufacturing methods including adhesion, mechanical fastening, welding, soldering, sealing, or other common methods to secure the components together. Such assemblies and manufacturing methods can substantially increase the cost of the electrode. It would be preferable, therefore, both economically and functionally, to manufacture the electrode as an integral device.

5. Objects

Accordingly, the general object of the present invention is to provide an electrode which has relatively inexpensive components and which can be assembled easily, efficiently, and economically. Such components also must assure signal integrity and be compatible with each other.

In order to achieve that general object, a more specific object is to provide an electrode which incorporates a conductive substrate as a connection point for signal transmission and as a mounting surface for transmission components. The conductive substrate is fused to compatible materials so that the components become integral parts of the conductive substrate. Thus, for example, the need for the expensive eyelet of the conventional stud electrode is eliminated.

One advantage of an integral electrode is minimization of the potential for signal degradation at interfaces. Another advantage is the reduction in manufacturing steps required, and consequent decreased cost, to form the integral electrode. Still another advantage is the reduction in the potential for assembly failure due to the reduced number of components required for assembly.

Rotational movement between the external connector (e.g., female snap connector) and the electrode may be necessary to provide a good electrical connection. Such connection must be assured even when the patient moves. It is another object of the present invention, therefore, to assure significant rotational movement between the external connector and the electrode.

A further object is to permit adaptation to the conventional lead wire plus female snap connector assemblies connected to most monitors and diagnostic equipment.

SUMMARY OF THE INVENTION

To achieve these and other objects, and in view of its purposes, the present invention provides an integral medical electrode which includes a fusible conductive substrate to which are fused other components, such as the conductor, of the electrode. The fusible conductive substrate has a non-conductive carrier providing a support layer; a conductive additive; and a sealant functioning as a fusible bonding medium to integrate the non-conductive carrier, the conductive additive, and the other components of the electrode.

A method of manufacturing the integral medical electrode of the present invention is also provided. That method includes the steps of providing a sealant in the solid state; converting the sealant from the solid state to a fluidic form; placing a non-conductive carrier, a conductive additive, and a conductor in the sealant while the sealant is in its fluidic form; and allowing the sealant to return to the solid state. Consequently, the sealant, non-conductive carrier, and conductive additive form a conductive substrate which is integrally fused to the conductor to form the integral medical electrode.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing, in which.

DETAILED DESCRIPTION OF THE INVENTION

Figure 1:
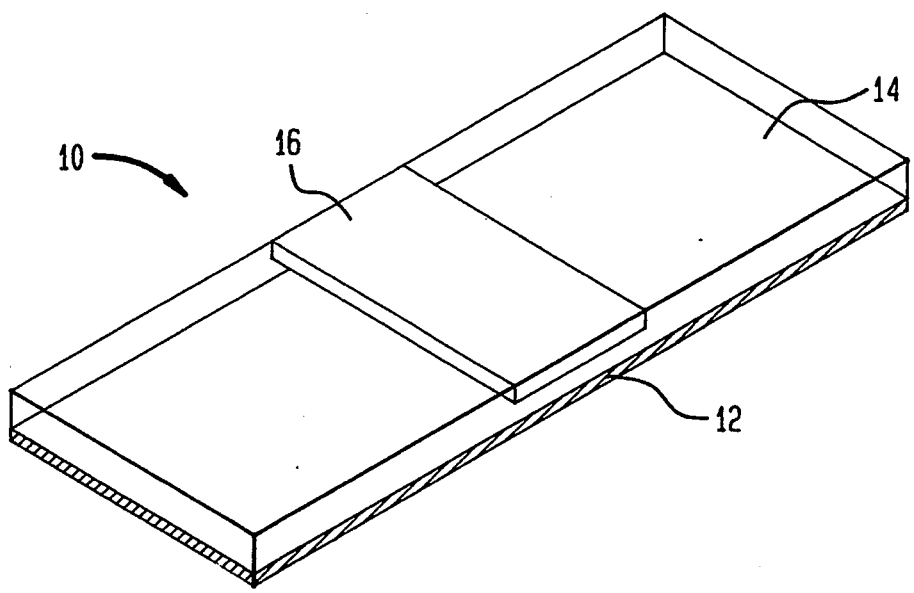
FIG. 1 is a perspective, partial cut-away view of the fusible conductive substrate according to the present invention.

Referring now to the drawing, wherein like reference numerals refer to like elements throughout, FIG. 1 shows the fusible conductive substrate 10 of the present invention. Although fusible substrate 10 may be formed as a rigid construction for some applications, it will typically be flexible. Fusible substrate 10 has a non-conductive carrier 12 as the support layer, a sealable material or sealant 14 as the fusible bonding medium, and a conductive additive 16 which provides conductivity while maintaining the fusible property of the fusible substrate 10. Non-conductive carrier 12 may be, for example, paper or a polymer film such as polyolefin, spun polyolefin, polyester, and urethane.

Fusible substrate 10 uses its characteristic of fusibility (or sealability) to achieve component attachment; it additionally functions as the carrier for the conductive additive 16. Thus, a distinct advantage of using fusible substrate 10 for component attachment is a reduction in the potential for assembly failure due to the reduced number of components required for assembly.

In discussing the present invention, "fusing" or "sealing" means a process whereby at least the surface of the material to be used as sealant 14 is temporarily converted from a solid state into fluidic form. In general, this can be accomplished by applying heat or chemical inducers to sealant 14. While sealant 14 is fluidic, supplemental processing of sealant 14 can be performed. Sealant 14 is then permitted to return to its solid state.

Materials suitable as sealant 14 include thermoplastics. Sealant 14 should have the following characteristics: the ability to melt without decomposition at the melting temperature, a glass transition temperature ($T_g$) below the temperature at which the device will be used (i.e., the sealant must be flexible at the temperature of use), and a low melt flow index (the material must flow when melted). Examples of thermoplastics which have those characteristics and, hence, are suitable as sealant 14 include: polyolefins, polyurethane elastomers, some nylons, plasticized polyvinyl chloride, copolymers of ethylene and acrylic acid, and some polymer blends.

In choosing the appropriate material for sealant 14, the characteristics outlined above should be considered. For example, polyethylene, which has a $T_g$ of $-20°$ C., would be preferred over polystyrene, which has a $T_g$ of about 93° C. and is brittle at room temperature. Similarly, polybutadiene ($T_g$ of $-73°$ C.) would be preferred over polyvinyl chloride ($T_g$ of 78° C.). One specific example of an appropriate material for sealant 14 is low density polyethylene (LDPE). A second specific example combines an LDPE base with a meltable coating applied to the base. LDPE has a melting point in the range between 105° and 120° C. The meltable coating is a copolymer of ethylene and acrylic acid, having a melting point of less than 100° C., which can be obtained from Michelman Inc. as "Michem 4983."

Fusible substrate 10 also includes a conductive additive 16 which provides conductivity while maintaining the fusible characteristics of sealant 14. Suitable materials for conductive additive 16 include any material or combination of materials with conductive properties which are compatible with sealant 14 as defined above. Conductive additive 16 may be added to sealant 14 to cover the outer surface of sealant 14. Alternatively, conductive additive 16 may be deposited within sealant 14. As conductive additive 16 is added to sealant 14, it may be drawn into a pre-determined pattern under, for example, the influence of a magnet.

Conductive additive 16 may be flakes or strips of metal materials such as silver, tin, and nickel. The metal salts, such as silver chloride, may be used in combination with the metal. Conductive alloys such as brass or copper nickel alloys may be suitable for certain applications. Other conductive materials, such as carbon, are also suitable as conductive additive 16. If the electrode is used for monitoring, which often mandates defibrillation, then a metal-metal salt combination such as silver-silver chloride may be required.

A balance between the conductivity provided to fusible substrate 10 by conductive additive 16 and the sealability provided by sealant 14 is extremely important. Fusible substrate 10 must provide a low-impedance path while fusing various components into an integral device. Accordingly, the ratio between the amount of conductive additive 16 and the amount of sealant 14 must be controlled carefully. For example, when 15% silver chloride is mechanically dispersed in silver flakes to form conductive additive 16, a ratio of 75% by weight conductive additive 16 to 25% by weight sealant 14 is suitable. The physical shape (e.g., the size of flakes, length and thickness of strips) of conductive additive 16 is also important to assure the appropriate balance between conductivity and sealability.

As it relates to the present invention, sealing can be accomplished by combining the components of the device while at least one element of sealant 14 is in fluidic form. The components are held together, in close proximity, while that element which is in fluidic form returns to the solid state. The result is a sealed, integral device.

It should be recognized that the invention is not limited to materials which are heat sealable; rather, chemically sealable materials may also be used to achieve the desired integral device. An integral device eliminates the requirement for multiple components at the electric signal interfaces and, accordingly, does not rely solely on the proximity of its components to assure signal integrity.

Figure 2A:
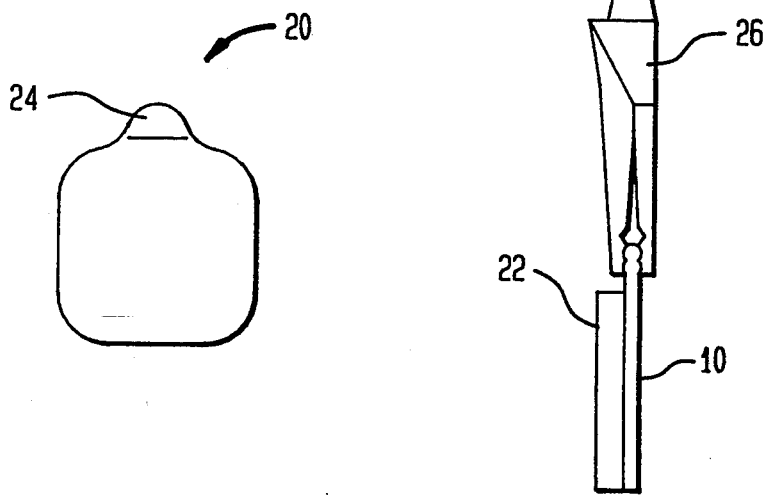
FIGS. 2A and 2B illustrate a tab-type electrode incorporating the fusible conductive substrate shown in FIG. 1.
Figure 2B:
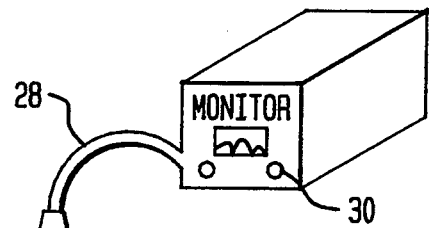

Referring to FIGS. 2A and 2B, fusible substrate 10 may be used to form an integral, tab-type electrode 20. Electrode 20 has a conductor 22 for receiving and transmitting bio-electric signals from the skin of a patient. Conductor 22 may be a solid gel, a conductive polymer, or other conductive medium. Conductor 22 is fused or bonded to conductive, fusible substrate 10 at the surface of fusible substrate 10 opposite non-conductive carrier 12.

As is known in the art, tab-type electrode 20 is formed in a shape which includes a tab 24. Tab 24 is easily engaged by an external electrical connector such as an alligator connector 26. Connector 26 receives the bioelectric signal from electrode 20 for transmission over a lead 28 to a monitor 30. Monitor 30 indicates, for example, the intensity and quality of the bio-electric signal emitted by the heart and transmitted through the skin. The type of monitor 30 which is suitable is within the knowledge of a person having ordinary skill in the art and will depend upon the intended use for electrode 20.

Figure 3A:
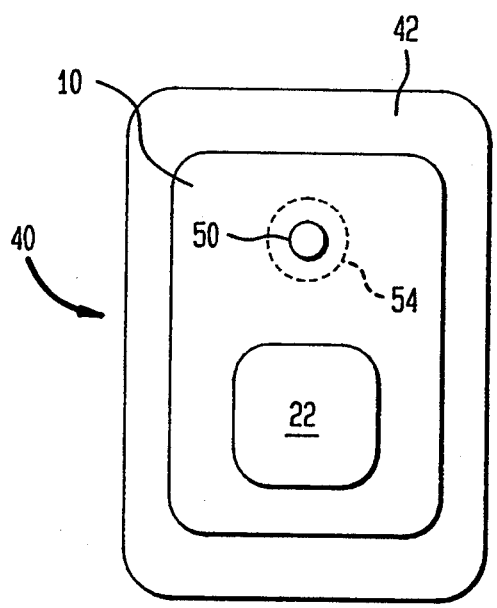
FIGS. 3A and 3B illustrate a stud-type electrode incorporating the fusible conductive substrate shown in FIG. 1.
Figure 3B:
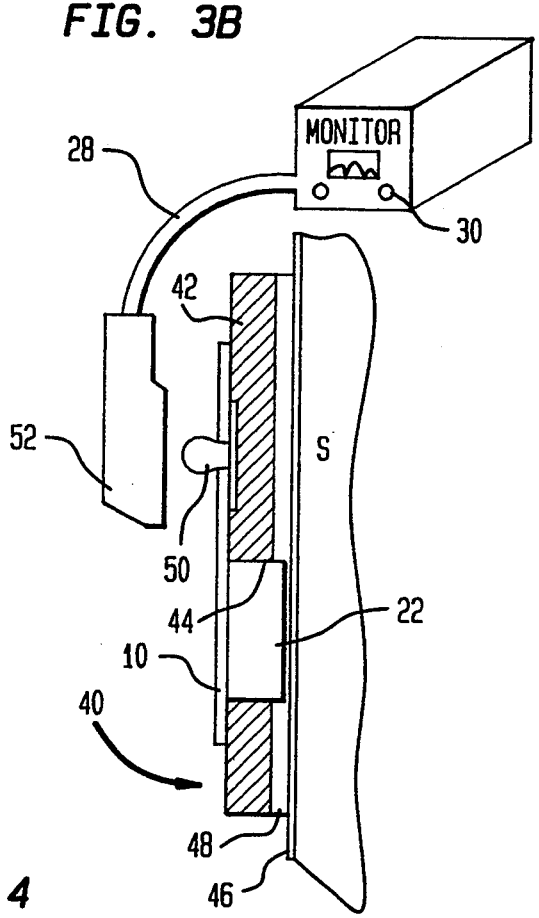

FIGS. 3A and 3B illustrate the preferred embodiment of the present invention. The stud-type electrode 40 illustrated in FIGS. 3A and 3B is significantly less complex than existing electrodes. Specifically, electrode 40 is an integral electrode.

Electrode 40 includes a non-conductive support layer 42 which provides support for the other components of electrode 40. Support layer 42 may be a foam pad having an aperture 44 either in its approximate center or, as shown, offset from its center. Conductor 22 is positioned within aperture 44 to transmit bio-electric signals from the skin, S, of the patient through support layer 42. Conductor 22 may substantially fill aperture 44 in support layer 42 to assure proper contact between conductor 22 and skin S when electrode 40 is affixed to skin S. An adhesive is attached to the bottom surface of support layer 42 so that conductor 22 is held against skin S.

A liner or cover sheet 46 covers support layer 42 and conductor 22 to protect support layer 42 and conductor 22, preclude premature adhesion, and prevent conductor 22 from drying. Liner 46 is a vapor barrier and has a release coating which covers the adhesive on the bottom surface of support layer 42. When electrode 40 is to be used, the release coating allows liner 46 to be peeled away.

Alternatively, as shown in FIGS. 3A and 3B, a conductive adhesive 48 may be applied to the bottom surfaces of conductor 22 and support layer 42. Conductive adhesive 48 is preferably a hydrogel. Liner 46 is then applied over conductive adhesive 48. Conductive adhesive 48 directly contacts skin S, after liner 46 is removed and electrode 40 is in use, and receives bio-electric signals from skin S.

A stud 50 is mounted to the top surface of support layer 42. Fusible substrate 10 is provided to integrate conductor 22, support layer 42, and stud 50—the essential components of electrode 40. A hole 54 is provided in fusible substrate 10 to accommodate stud 50. Integration is accomplished as described above. Because fusible substrate 10 is conductive, it provides an electrical path from conductor 22 to stud 50. A conventional female snap connector 52 can engage stud 50 and receive the electrical signal from stud 50. Lead 28 then carries that signal from female snap connector 52 to monitor 30.

Thus, the bio-electric signal found in skin S is received by conductive adhesive 48; transmitted through support layer 42 by conductor 22; carried to stud 50 by conductive, fusible substrate 10 where it is delivered to female snap connector 52; and, finally, transmitted to monitor 30 along lead 28.

When manufacturing a conventional stud-type electrode, an opening is formed in the support layer. A relatively expensive eyelet is inserted into that opening. Then the stud is mechanically fastened, such as by crimping, to the eyelet. The conventional manufacturing steps used to attach the stud and eyelet to the support layer include a step and repeat process.

In contrast, electrode 40 of the present invention eliminates the need for an eyelet. In addition, the manufacturing steps used to form electrode 40 do not require a break in the manufacturing process. Rather, the process used to manufacture electrode 40 is continuous.

Specifically, sealant 14 and conductive additive 16 may be combined with a liquid (e.g., water) to form a dispersion mixture. Non-conductive carrier 12 is coated with the dispersion mixture to form, upon evaporation of the liquid, fusible substrate 10. Hole 54 is then punched through fusible substrate 10 and stud 50 is placed in hole 54. Fusible substrate 10, with stud 50, is placed over support layer 42. Subsequently, sealant 14 in fusible substrate 10 is activated by heat or chemical reaction. Sealant 14 is in its fluidic form, following activation, and will flow to engage the components of electrode 40. When sealant 14 returns to its solid state, an integral, fused electrode 40 results.

Figure 4:
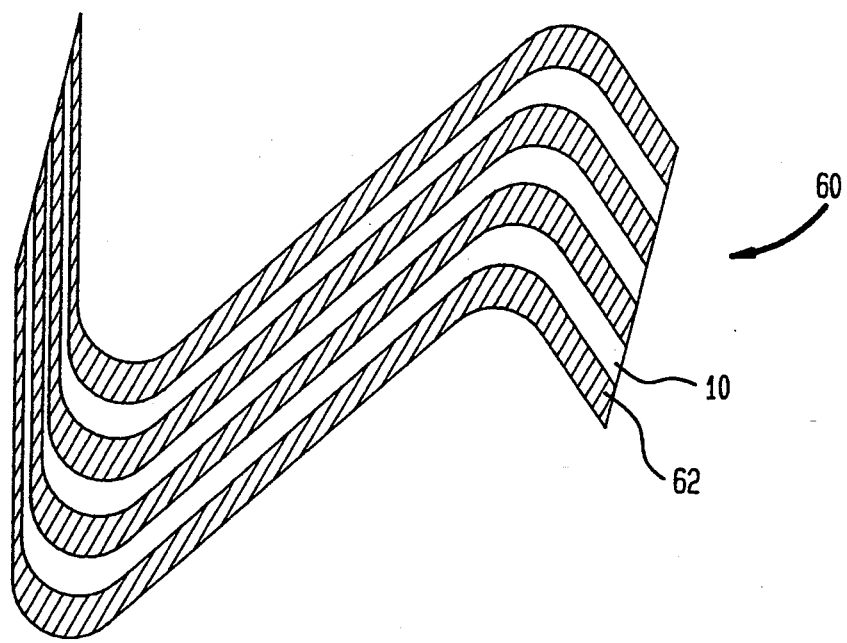
FIG. 4 illustrates a flexible, electrically conductive ribbon connector formed using the fusible conductive substrate shown in FIG. 1.

FIG. 4 shows another application for fusible substrate 10. Fusible substrate 10 may be fused or bonded to a non-conductive carrier 62 to form a flexible, electrically conductive ribbon connector 60. As shown in FIG. 4, fusible substrate 10 and non-conductive carrier 62 may be alternated in layers to form ribbon connector 60. Non-conductive carrier 62 functions as a support layer for ribbon connector 60.

Figure 5A:
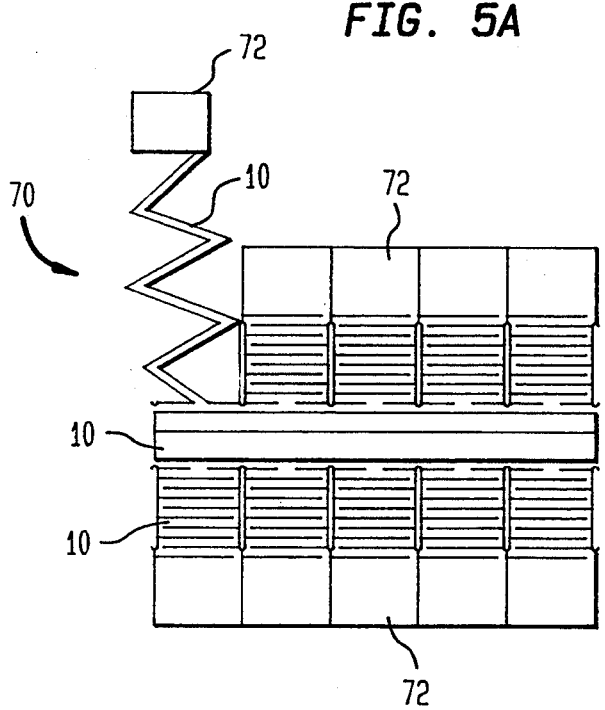
FIGS. 5A and 5B depict a complex electrode manifold incorporating the fusible conductive substrate shown in FIG. 1.
Figure 5B:
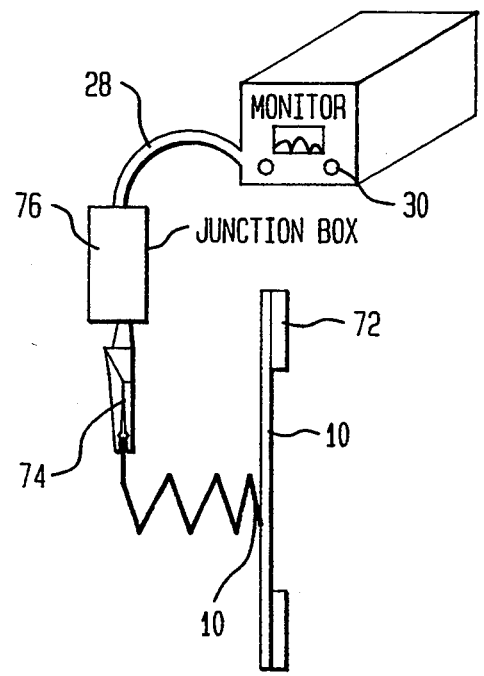

FIGS. 5A and 5B depict a complex electrode manifold 70 for use in measuring bio-potentials. Electrode manifold 70 includes multiple skin-contacting conductive pads 72, typically formed in sheets of separable pads 72. Each conductive pad 72 may be electrically and physically interconnected to electrode manifold 70 through fusible substrate 10. Flexible electric ribbon connector 60, as shown in FIG. 4, is also suitable for connecting conductive pads 72 to electrode manifold 70.

An alligator-type multi-connector 74 engages fusible substrate 10 and receives the electric signal transmitted by fusible substrate 10. That signal is transmitted, in turn, from multi-connector 74 to a junction box 76 and then by lead 28 to monitor 30. Thus, electrode manifold 70 allows one connection to a number (ten are illustrated in FIG. 5A) of electrode pads 72.

Electrode manifold 70 offers several important advantages attributable to the flat configuration made possible by fusible substrate 10. A flat configuration is desirable because it simplifies manufacture, eases packaging and transport, protects electrode manifold 70 from damage, and facilitates use of electrode manifold 70 on the skin of the patient.

Figure 6A:
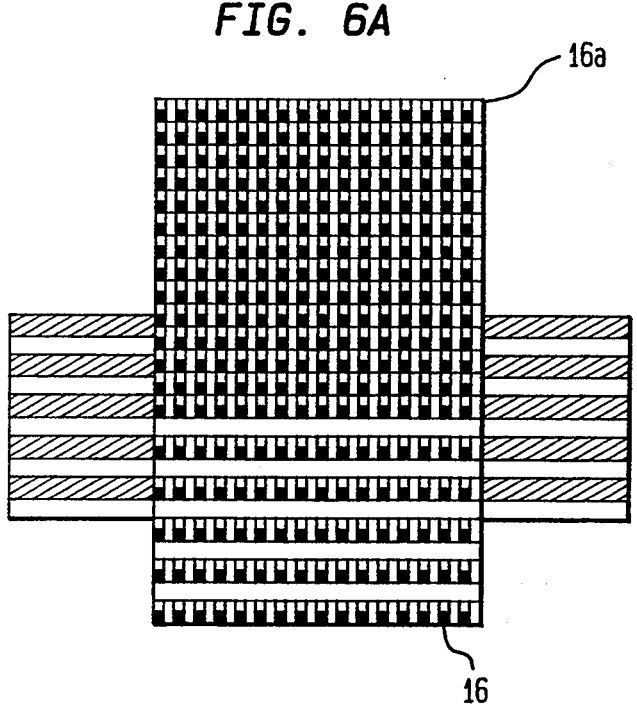
FIGS. 6A and 6B illustrate the process of drawing the conductive additive of the fusible conductive substrate shown in FIG. 1 into a pre-determined pattern under the influence of a magnet.
Figure 6B:
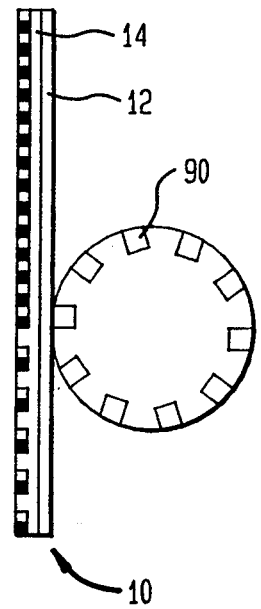

As mentioned above, conductive additive 16 may be drawn into a pre-determined pattern as it is added to sealant 14 to form fusible substrate 10. If conductive additive 16 is a magnetic material, such a nickel, the pattern may be induced by the influence of a magnetic force. FIGS. 6A and 6B illustrate that process. A non-conductive carrier 12 is provided as a support layer. Sealant 14 is bonded to non-conductive carrier 12, as described above. Conductive additive 16 is then ready for bonding to sealant 14 to form fusible substrate 10.

A magnetic template 90, able to induce the desired pattern of conductive additive 16 in fusible substrate 10, is positioned adjacent fusible substrate 10. The pattern of conductive additive 16a (e.g., nickel) before fusible substrate 10 is influenced by the application of magnetic template 90 is shown. Also shown in FIGS. 6A and 6B is the pattern of conductive additive 16 after application of the magnetic influence has induced the desired pattern.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention. Specifically, although the present invention focuses on monitoring and diagnostic electrodes and, more particularly, on stud-type monitoring and diagnostic electrodes, the fusible substrate disclosed can be incorporated in a variety of electrode devices.

What is claimed:

1. An integral medical electrode adapted to contact the skin of a patient and comprising:
   a conductor transmitting bio-electric signals between the skin and the conductor; and
   a conductive substrate having:
   (a) a non-conductive carrier providing a support layer,
   (b) a conductive additive, and
   (c) a sealant sealing, fusing, and bonding said non-conductive carrier, said conductive additive, and said conductor into said integral medical electrode.

2. The electrode as claimed in claim 1 wherein said sealant is a thermoplastic.

3. The electrode as claimed in claim 2 wherein said thermoplastic sealant is selected from the group consisting of polyolefins, polyurethane elastomers, nylons, plasticized polyvinyl chloride, copolymers of ethylene and acrylic acid, and polymer blends.

4. The electrode as claimed in claim 3 wherein said thermoplastic sealant is a low density polyethylene base coated with an ethylene and acrylic acid copolymer.

5. The electrode as claimed in claim 1 wherein said sealant has an inducer selected from the group consisting of heat and chemical inducers adapted to temporarily convert said sealant from a solid state into fluidic form.

6. The electrode as claimed in claim 1 wherein said conductive additive is selected from the group consisting of metals, metal alloys, metal-metal salt combinations, and carbon.

7. The electrode as claimed in claim 1 wherein said non-conductive carrier is selected from the group consisting of paper and polymer films.

8. The electrode as claimed in claim 1 wherein said conductive additive is fused to said sealant and becomes an element of said substrate in a predetermined pattern.

9. The electrode as claimed in claim 1 wherein said electrode is adapted for monitoring and diagnostic applications and said conductor receives and transmits bio-electric signals from the skin, said electrode further comprising a stud sealed, fused, and bonded to said substrate by said sealant and adapted to engage a female snap connector electrically interconnected through a lead to a monitor, said substrate forming an electrical path from said conductor to said stud.

10. The electrode as claimed in claim 9 further comprising a non-conductive support layer sealed, fused, and bonded to said substrate by said sealant and supporting said substrate, said conductor, and said stud.

11. The electrode as claimed in claim 10 wherein said support layer has an aperture and said conductor substantially fills said aperture to assure contact between said conductor and the skin.

12. The electrode as claimed in claim 11 further comprising an adhesive, said support layer having a bottom surface to which said adhesive is attached to hold said conductor against the skin.

13. The electrode as claimed in claim 12 further comprising a liner covering said support layer and said conductor when said electrode is not in use.

14. The electrode as claimed in claim 12 further comprising a conductive adhesive, said support layer and said conductor each having a bottom surface to which said conductive adhesive is attached to hold said conductor in electrical contact against the skin.

15. The electrode as claimed in claim 14 further comprising a liner covering said conductive adhesive when said electrode is not in use.

16. An integral medical electrode adapted to contact the skin of a patient, adapted for monitoring and diagnostic applications, and comprising:
a conductor receiving and transmitting bio-electric signals from the skin; and
a conductive substrate having:
(a) a non-conductive carrier providing a support layer,
(b) a conductive additive, and
(c) a sealant sealing, fusing, and bonding said non-conductive carrier, said conductive additive, and said conductor into said integral medical electrode,
said conductive substrate having a shape which includes a tab adapted to engage an electrical connector electrically interconnected through a lead to a monitor.

17. The electrode as claimed in claim 16 wherein said sealant is a thermoplastic.

18. The electrode as claimed in claim 17 wherein said thermoplastic sealant is selected from the group consisting of polyolefins, polyurethane elastomers, nylons, plasticized polyvinyl chloride, copolymers of ethylene and acrylic acid, and polymer blends.

19. The electrode as claimed in claim 18 wherein said thermoplastic sealant is a low density polyethylene base coated with an ethylene and acrylic acid copolymer.

20. The electrode as claimed in claim 16 wherein said sealant has an inducer selected from the group consisting of heat and chemical inducers adapted to temporarily convert said sealant from a solid state into fluidic form.

21. The electrode as claimed in claim 16 wherein said conductive additive is selected from the group consisting of metals, metal alloys, metal-metal salt combinations, and carbon.

22. The electrode as claimed in claim 16 wherein said non-conductive carrier is selected from the group consisting of paper and polymer films.

23. The electrode as claimed in claim 16 wherein said conductive additive is fused to said sealant and becomes an element of said substrate in a predetermined pattern.

24. An integral medical electrode adapted to contact the skin of a patient, adapted for monitoring and diagnostic applications, and comprising:
a non-conductive support layer;
a conductor supported by said support layer and receiving and transmitting bio-electric signals from the skin;
a stud supported by said support layer and adapted to engage a female snap connector electrically interconnected through a lead to a monitor;
a conductive substrate supported by said support layer, forming an electrical path from said conductor to said stud, and having:
(a) a non-conductive carrier providing a support layer,
(b) a conductive additive, and
(c) a sealant sealing, fusing, and bonding said non-conductive carrier, said conductive additive, said stud, said support layer, and said conductor into said integral medical electrode.

25. The electrode as claimed in claim 24 wherein said sealant is a thermoplastic.

26. The electrode as claimed in claim 25 wherein said thermoplastic sealant is selected from the group consisting of polyolefins, polyurethane elastomers, nylons, plasticized polyvinyl chloride, copolymers of ethylene and acrylic acid, and polymer blends.

27. The electrode as claimed in claim 26 wherein said thermoplastic sealant is a low density polyethylene base coated with an ethylene and acrylic acid copolymer.

28. The electrode as claimed in claim 24 wherein said sealant has an inducer selected from the group consisting of heat and chemical inducers adapted to temporarily convert said sealant from a solid state into fluidic form.

29. The electrode as claimed in claim 24 wherein said conductive additive is selected from the group consisting of metals, metal alloys, metal-metal salt combinations, and carbon.

30. The electrode as claimed in claim 24 wherein said non-conductive carrier is selected from the group consisting of paper and polymer films.

31. The electrode as claimed in claim 24 wherein said conductive additive is sealed, fused, and bonded to said sealant and becomes an element of said substrate in a pre-determined pattern.

* * * * *

UNITED STATES PATENT AND TRADEMARK OFFICE
CERTIFICATE OF CORRECTION

PATENT NO.   : 5,400,782
DATED        : March 28, 1995
INVENTOR(S)  : Michael K. Beaubiah It is certified that error appears in the above-identified patent and that said Letters Patent is hereby corrected as shown below:

Column 9, line 18 (first line of claim 14), delete "12" and insert --11--.

Signed and Sealed this

Twenty-seventh Day of June, 1995

Attest:

BRUCE LEHMAN

Attesting Officer

Commissioner of Patents and Trademarks